United States Patent
Lauffer et al.

(10) Patent No.: US 6,528,533 B2
(45) Date of Patent: Mar. 4, 2003

(54) AZO AMINO ACIDS DERIVATIVES

(75) Inventors: David Lauffer, Stow, MA (US); Michael Mullican, Needham, MA (US)

(73) Assignee: Vertex Pharmaceuticals, Incorporated, Cambridge, MA (US)

( * ) Notice: Subject to any disclaimer, the term of this patent is extended or adjusted under 35 U.S.C. 154(b) by 0 days.

(21) Appl. No.: 10/039,900

(22) Filed: Jan. 3, 2002

(65) Prior Publication Data

US 2002/0103190 A1 Aug. 1, 2002

Related U.S. Application Data

(63) Continuation of application No. PCT/US00/18416, filed on Jul. 5, 2000.
(60) Provisional application No. 60/142,569, filed on Jul. 6, 1999.

(51) Int. Cl.[7] .................. A61K 44/4436; C07D 213/53; C07D 213/56; C07D 216/56
(52) U.S. Cl. ........................ 514/357; 546/329; 546/332; 546/340
(58) Field of Search ................................. 546/329, 332, 546/340; 514/357

(56) References Cited

FOREIGN PATENT DOCUMENTS

| WO | WO 96/41609 | 12/1996 |
|----|----|----|
| WO | WO 99/10340 | 3/1999 |

OTHER PUBLICATIONS

Hamilton, G. S., et al., "FKBP12–Binding Domain Analogues of FK506 Are Potent, Non–immunosuppressive Neurotrophic Agents In–Vitro And Promote Recovery In A Mouse Of Parkinson's Disease," *Bioorg. Med. Chem. Lett.*, vol. 7, No. 13, pp. 1785–90 (1997).

*Primary Examiner*—Ceila Chang
*Assistant Examiner*—Rita Desai
(74) *Attorney, Agent, or Firm*—Vertex Pharmaceuticals, Incorporated

(57) ABSTRACT

The present invention relates to azo amino acid derivatives for treating or preventing neuronal damage associated with neurological diseases. The invention also provides compositions comprising the compounds of the present invention and methods of utilizing those compositions for treating or preventing neuronal damage.

12 Claims, No Drawings

AZO AMINO ACIDS DERIVATIVES

CROSS-REFERENCE TO RELATED APPLICATIONS

This application is a continuing application of co-pending International Patent Application PCT/US00/18416, filed Jul. 5, 2000, which claims priority of U.S. provisional patent No. 60/142,569, filed Jul. 6, 1999.

TECHNICAL FIELD OF THE INVENTION

The present invention relates to azo amino acid derivatives for treating or preventing neuronal damage associated with neurological diseases. The invention also provides compositions comprising the compounds of the present invention and methods of utilizing those compositions for treating or preventing neuronal damage.

BACKGROUND OF THE INVENTION

Neurological diseases are associated with the death of or injury to neuronal cells. Typical treatment of neurological diseases involves drugs capable of inhibiting neuronal cell death. A more recent approach involves the promotion of nerve regeneration by promoting neuronal growth.

Neuronal growth, which is critical for the survival of neurons, is stimulated in vitro by nerve growth factors (NGF). For example, Glial Cell Line-Derived Neurotrophic Factor (GDNF) demonstrates neurotrophic activity both, in vivo and in vitro, and is currently being investigated for the treatment of Parkinson's disease. Insulin and insulin-like growth factors have been shown to stimulate growth of neurites in rat pheochromocytoma PC12 cells and in cultured sympathetic and sensory neurons [Recio-Pinto et al., *J. Neurosci.*, 6, pp. 1211–1219 (1986)]. Insulin and insulin-like growth factors also stimulate the regeneration of injured motor nerves in vivo and in vitro [Near et al., *Proc. Natl. Acad. Sci.*, pp. 89, 11716–11720 (1992); and Edbladh et al., *Brain Res.*, 641, pp. 76–82 (1994)]. Similarly, fibroblast growth factor (FGF) stimulates neural proliferation [D. Gospodarowicz et al., *Cell Differ.*, 19, p. 1 (1986)] and growth [M. A. Walter et al., *Lymphokine Cytokine Res.*, 12, p. 135 (1993)].

There are, however, several disadvantages associated with the use of nerve growth factors for treating neurological diseases. They do not readily cross the blood-brain barrier. They are unstable in plasma and they have poor drug delivery properties.

Recently, small molecules have been shown to stimulate neurite outgrowth in vivo. In individuals suffering from a neurological disease, this stimulation of neuronal growth protects neurons from further degeneration, and accelerates the regeneration of nerve cells. For example, estrogen has been shown to promote the growth of axons and dendrites, which are neurites sent out by nerve cells to communicate with each other in a developing or injured adult brain [(C. Dominique Toran-Allerand et al., *J. Steroid Biochem. Mol. Biol.*, 56, pp. 169–78 (1996); and B. S. McEwen et al., *Brain Res. Dev. Brain. Res.*, 87, pp. 91–95 (1995)]. The progress of Alzheimer's disease is slowed in women who take estrogen. Estrogen is hypothesized to complement NGF and other neurotrophins and thereby help neurons differentiate and survive.

Other target sites for the treatment of neurodegenerative disease are the immunophilin class of proteins. Immunophilins are a family of soluble proteins that mediate the actions of immunosuppressant drugs such as cyclosporin A, FK506 and rapamycin. Of particular interest is the 12 kDa immunophilin, FK-506 binding protein (FKBP12). FKBP12 binds FK-506 and rapamycin, leading to an inhibition of T-cell activation and proliferation. Interestingly, the mechanism of action of FK-506 and rapamycin are different. For a review, see, S. H. Solomon et al., *Nature Med.*, 1, pp. 32–37 (1995). It has been reported that compounds with an affinity for FKBP12 that inhibit that protein's rotamase activity possess nerve growth stimulatory activity. [Lyons et al., *Proc. Natl. Acad. Sci. USA*, 91, pp. 3191–3195 (1994)]. Many of these such compounds also have immunosuppressive activity.

FK506 (Tacrolimus) has been demonstrated to act synergistically with NGF in stimulating neurite outgrowth in PC12 cells as well as sensory ganglia [Lyons et al. (1994)]. This compound has also been shown to be neuroprotective in focal cerebral ischemia [J. Sharkey and S. P. Butcher, *Nature*, 371, pp. 336–339 (1994)] and to increase the rate of axonal regeneration in injured sciatic nerve [B. Gold et al., *J. Neurosci.*, 15, pp. 7509–16 (1995)].

The use of immunosuppressive compounds, however, has drawbacks in that prolonged treatment with these compounds can cause nephrotoxicity [Kopp et al., *J. Am. Soc. Nephrol.*, 1, p. 162 (1991)], neurological deficits [P. C. DeGroen et al., *N. Eng. J. Med.*, 317, p. 861 (1987)] and vascular hypertension [Kahan et al., *N. Eng. J. Med.*, 321, p. 1725 (1989)].

More recently, sub-classes of FKBP binding compounds which inhibit rotomase activity, but which purportedly lack immunosuppressive function have been disclosed for use in stimulating nerve growth [see, U.S. Pat. No. 5,614,547; WO 96/40633; WO 96/40140; WO 97/16190; J. P. Steiner et al., *Proc. Natl. Acad. Sci. USA*, 94, pp. 2019–23 (1997); and G. S. Hamilton et al., *Bioorg. Med. Chem. Lett.*, 7, pp. 1785–90 (1997)].

Stimulation of neural axons in nerve cells by piperidine derivatives is described in WO 96/41609. Clinical use of the piperidine and pyrrolidine derivatives known so far for stimulating axonal growth has not been promising, as the compounds are unstable in plasma and do not pass the blood-brain barrier in adequate amounts.

Though a wide variety of neurological degenerative diseases may be treated by promoting repair of neuronal damage, there are relatively few agents known to possess these properties. Thus, there remains a need for new compounds and compositions that have the ability to either prevent or treat neuronal damage associated with neuropathological diseases.

SUMMARY OF THE INVENTION

The present invention provides compounds having formula (I):

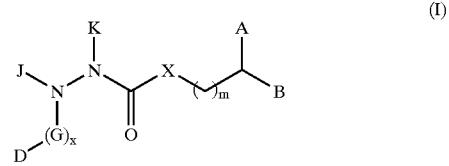

and pharmaceutically acceptable derivatives thereof, wherein:

X is O, S, $NR^1$ or $C(R^1)_2$

A, B and $R^1$ are independently E, $(C_1–C_{10})$-straight or branched alkyl, $(C_2–C_{10})$-straight or branched alkenyl or alkynyl, or ($C_5$–$C_7$)-cycloalkyl or cycloalkenyl; wherein 1 or 2 hydrogen atoms in said alkyl, alkenyl or alkynyl are optionally and independently replaced with E, ($C_5$–$C_7$)-cycloalkyl or cycloalkenyl; and wherein 1 to 2 of the —$CH_2$— groups in said alkyl, alkenyl, or alkynyl groups is optionally and independently replaced by —O—, —S—, —S(O)—, —S(O)$_2$—, =N—, —N= or —N($R^3$)—;

or B and $R^1$ are independently hydrogen;

wherein $R^3$ is selected from hydrogen, ($C_1$–$C_4$)-straight or branched alkyl, ($C_3$–$C_4$)-straight or branched alkenyl or alkynyl, or ($C_1$–$C_4$) bridging alkyl, wherein a bridge is formed between the nitrogen atom to which said $R^3$ is bound and any carbon atom of said alkyl, alkenyl or alkynyl to form a ring, and wherein said ring is optionally benzofused;

wherein E is a saturated, partially saturated or unsaturated, or aromatic monocyclic or bicyclic ring system, wherein each ring comprises 5 to 7 ring atoms independently selected from C, N, O or S; and wherein no more than 4 ring atoms are selected from N, O or S;

wherein 1 to 4 hydrogen atoms in E are optionally and independently replaced with halogen, hydroxyl, hydroxymethyl, nitro, $SO_3H$, trifluoromethyl, trifluoromethoxy, ($C_1$–$C_6$)-straight or branched alkyl, ($C_2$–$C_6$)-straight or branched alkenyl, O—[($C_1$–$C_6$)-straight or branched alkyl], O—[($C_3$–$C_6$)-straight or branched alkenyl], ($CH_2$)$_n$—N($R^4$)($R^5$), ($CH_2$)$_n$—NH($R^4$)-($CH_2$)$_n$—Z, ($CH_2$)$_n$—N($R^4$—($CH_2$)$_n$—Z)($R^5$—($CH_2$)$_n$—Z), ($CH_2$)$_n$—Z, O—($CH_2$)$_n$—Z, ($CH_2$)$_n$—O—Z, S—($CH_2$)$_n$—Z, CH=CH—Z, 1,2-methylenedioxy, C(O)OH, C(O)O—[($C_1$–$C_6$)-straight or branched alkyl], C(O)O—($CH_2$)$_n$—Z or C(O)—N($R^4$)($R^5$);

wherein each of $R^4$ and $R^5$ are independently hydrogen, ($C_1$–$C_6$)-straight or branched alkyl, ($C_3$–$C_5$)-straight or branched alkenyl, or wherein $R^4$ and $R^5$, when bound to the same nitrogen atom, are taken together with the nitrogen atom to form a 5 or 6 membered ring, wherein said ring optionally contains 1 to 3 additional heteroatoms independently selected from N, O or S; wherein said alkyl, alkenyl or alkynyl groups in $R_4$ and $R_5$ are optionally substituted with Z.

each n is independently 0 to 4;

each Z is independently selected from a saturated, partially saturated or unsaturated, monocyclic or bicyclic ring system, wherein each ring comprises 5 to 7 ring atoms independently selected from C, N, O or S; and wherein no more than 4 ring atoms are selected from N, O or S;

wherein 1 to 4 hydrogen atoms in Z are optionally and independently replaced with halo, hydroxy, nitro, cyano, C(O)OH, ($C_1$–$C_3$)-straight or branched alkyl, O—($C_1$–$C_3$)-straight or branched alkyl, C(O)O—[($C_1$–$C_3$)-straight or branched alkyl], amino, NH[($C_1$–$C_3$)-straight or branched alkyl], or N—[($C_1$–$C_3$)-straight or branched alkyl]$_2$;

J and K are independently selected from hydrogen, ($C_1$–$C_6$)-straight or branched alkyl, ($C_2$–$C_6$)-straight or branched alkenyl or alkynyl, or cyclohexylmethyl, wherein 1 to 2 hydrogen atoms in said alkyl, alkenyl or alkynyl is optionally and independently replaced with E;

provided that J and K are not simultaneously hydrogen;

wherein J and K are optionally and independently substituted with up to 3 substituents selected from halogen, OH, O—($C_1$–$C_6$)-alkyl, O—($CH_2$)$_n$—Z, $NO_2$, C(O)OH, C(O)—O—($C_1$–$C_6$)-alkyl, C(O)N$R^4R^5$, N$R^4R^5$ and ($CH_2$)$_n$—Z; or, K taken together with one of J or $R^1$ forms a 5–7 membered saturated or unsaturated heterocyclic ring, optionally containing up to 3 additional heteroatoms selected from O, N, S and S(O$_2$), wherein 1 to 4 hydrogen atoms in said heterocyclic ring are optionally and independently replaced with ($C_1$–$C_6$)-straight or branched alkyl, ($C_2$–$C_6$)-straight or branched alkenyl or alkynyl, oxo, hydroxyl or Z; and wherein any —$CH_2$— group said heterocyclic ring is optionally and independently replaced by —O—, —S—, —S(O)—, —S(O$_2$)—, or —N($R^3$)—; and wherein said heterocyclic ring is optionally fused with E;

G, when present, is —S(O)$_2$—, —C(O)—, —S(O)$_2$—Y—, —C(O)—Y—, —C(O)—C(O)—, or —C(O)—C(O)—Y—;

Y is oxygen, or N($R^6$);

wherein $R^6$ is hydrogen, E, ($C_1$–$C_6$)-straight or branched alkyl, ($C_3$–$C_6$)-straight or branched alkenyl or alkynyl; or wherein $R^6$ and D are taken together with the atoms to which they are bound to form a 5 to 7 membered ring system wherein said ring optionally contains 1 to 3 additional heteroatoms independently selected from O, S, N, NH, SO, or SO$_2$; and wherein said ring is optionally benzofused;

D is hydrogen, ($C_1$–$C_7$)-straight or branched alkyl, ($C_2$–$C_7$)-straight or branched alkenyl or alkynyl, ($C_5$–$C_7$)-cycloalkyl or cycloalkenyl optionally substituted with ($C_1$–$C_6$)-straight or branched alkyl or ($C_2$–$C_7$)-straight or branched alkenyl or alkynyl, [($C_1$–$C_7$)-alkyl]-E, [($C_2$–$C_7$)-alkenyl or alkynyl]-E, or E;

wherein 1 to 2 of the $CH_2$ groups of said alkyl, alkenyl or alkynyl chains in D is optionally replaced by —O—, —S—, —S(O)—, —S(O$_2$)—, or —N($R^3$);

m is 0 to 3; and x is 0 or 1;

provided that when J is hydrogen or G is selected from —S(O)$_2$—, C(O)C(O)—, SO$_2$—Y, C(O)—Y, or C(O)C(O)—Y, wherein Y is O; then D is not hydrogen.

In another embodiment, the invention provides pharmaceutical compositions comprising the compounds of formula (I). These compositions may be utilized in methods treating various neurological diseases which are influenced by neuronal regeneration and axon growth or for stimulating neuronal regeneration in an ex vivo nerve cell. Examples of such diseases include peripheral nerve destruction due to physical injury or diseases such as diabetes; physical injuries to the central nervous system (e.g., brain or spinal cord); stroke; neurological disturbances due to nerve degeneration, such as Parkinson's disease, Alzheimer's disease, and amylotrophic lateral sclerosis.

DETAILED DESCRIPTION OF THE INVENTION

The present invention provides compounds having formula (I):

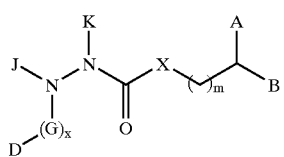

(I)

and pharmaceutically acceptable derivatives thereof, wherein:

X is O, S, NR$^1$ or C(R$^1$)$_2$

A, B and R$^1$ are independently E, (C$_1$–C$_{10}$)-straight or branched alkyl, (C$_2$–C$_{10}$)-straight or branched alkenyl or alkynyl, or (C$_5$–C$_7$)-cycloalkyl or cycloalkenyl; wherein 1 or 2 hydrogen atoms in said alkyl, alkenyl or alkynyl are optionally and independently replaced with E, (C$_5$–C$_7$)-cycloalkyl or cycloalkenyl; and wherein 1 to 2 of the —CH$_2$— groups in said alkyl, alkenyl, or alkynyl groups is optionally and independently replaced by —O—, —S—, —S(O)—, —S(O)$_2$—, =N—, —N= or —N(R$^3$)—;

or B and R$^1$ are independently hydrogen;

wherein R$^3$ is selected from hydrogen, (C$_1$–C$_4$)-straight or branched alkyl, (C$_3$–C$_4$)-straight or branched alkenyl or alkynyl, or (C$_1$–C$_4$) bridging alkyl, wherein a bridge is formed between the nitrogen atom to which said R$^3$ is bound and any carbon atom of said alkyl, alkenyl or alkynyl to form a ring, and wherein said ring is optionally benzofused;

wherein E is a saturated, partially saturated or unsaturated, or aromatic monocyclic or bicyclic ring system, wherein each ring comprises 5 to 7 ring atoms independently selected from C, N, O or S; and wherein no more than 4 ring atoms are selected from N, O or S;

wherein 1 to 4 hydrogen atoms in E are optionally and independently replaced with halogen, hydroxyl, hydroxymethyl, nitro, SO$_3$H, trifluoromethyl, trifluoromethoxy, (C$_1$–C$_6$)-straight or branched alkyl, (C$_2$–C$_6$)-straight or branched alkenyl, O—[(C$_1$–C$_6$)-straight or branched alkyl], O—[(C$_3$–C$_6$)-straight or branched alkenyl], (CH$_2$)$_n$—N(R$^4$)(R$^5$), (CH$_2$)$_n$—NH(R$^4$)—(CH$_2$)$_n$—Z, (CH$_2$)$_n$—N(R$^4$—(CH$_2$)$_n$—Z)(R$^5$—(CH$_2$)$_n$—Z), (CH$_2$)$_n$—Z, O—(CH$_2$)$_n$—Z, (CH$_2$)$_n$—O—Z, S—(CH$_2$)$_n$—Z, CH=CH—Z, 1,2-methylenedioxy, C(O)OH, C(O)O—[(C$_1$–C$_6$)-straight or branched alkyl], C(O)O—(CH$_2$)$_n$—Z or C(O)—N(R$^4$)(R$^5$);

wherein each of R$^4$ and R$^5$ are independently hydrogen, (C$_1$–C$_6$)-straight or branched alkyl, (C$_3$–C$_5$)-straight or branched alkenyl, or wherein R$^4$ and R$^5$, when bound to the same nitrogen atom, are taken together with the nitrogen atom to form a 5 or 6 membered ring, wherein said ring optionally contains 1 to 3 additional heteroatoms independently selected from N, O or S; wherein said alkyl, alkenyl or alkynyl groups in R$_4$ and R$_5$ are optionally substituted with Z.

each n is independently 0 to 4;

each Z is independently selected from a saturated, partially saturated or unsaturated, monocyclic or bicyclic ring system, wherein each ring comprises 5 to 7 ring atoms independently selected from C, N, O or S; and wherein no more than 4 ring atoms are selected from N, O or S;

wherein 1 to 4 hydrogen atoms in Z are optionally and independently replaced with halo, hydroxy, nitro, cyano, C(O)OH, (C$_1$–C$_3$)-straight or branched alkyl, O—(C$_1$–C$_3$)-straight or branched alkyl, C(O)O—[(C$_1$–C$_3$)-straight or branched alkyl], amino, NH[(C$_1$–C$_3$)-straight or branched alkyl], or N—[(C$_1$–C$_3$)-straight or branched alkyl]$_2$;

J and K are independently selected from hydrogen, (C$_1$–C$_6$)-straight or branched alkyl, (C$_2$–C$_6$)-straight or branched alkenyl or alkynyl, or cyclohexylmethyl, wherein 1 to 2 hydrogen atoms in said alkyl, alkenyl or alkynyl is optionally and independently replaced with E; provided that J and K are not simultaneously hydrogen;

wherein J and K are optionally and independently substituted with up to 3 substituents selected from halogen, OH, O—(C$_1$–C$_6$)-alkyl, O—(CH$_2$)$_n$—Z, NO$_2$, C(O)OH, C(O)—O—(C$_1$–C$_6$)-alkyl, C(O)NR$^4$R$^5$, NR$^4$R$^5$ and (CH$_2$)$_n$—Z; or, K taken together with one of J or R$^1$ forms a 5–7 membered saturated or unsaturated heterocyclic ring, optionally containing up to 3 additional heteroatoms selected from O, N, S and S(O$_2$), wherein 1 to 4 hydrogen atoms in said heterocyclic ring are optionally and independently replaced with (C$_1$–C$_6$)-straight or branched alkyl, (C$_2$–C$_6$)-straight or branched alkenyl or alkynyl, oxo, hydroxyl or Z; and wherein any —CH$_2$— group said heterocyclic ring is optionally and independently replaced by —O—, —S—, —S(O)—, —S(O$_2$)—, or —N(R$^3$)—; and wherein said heterocyclic ring is optionally fused with E;

G, when present, is —S(O)$_2$—, —C(O)—, —S(O)$_2$—Y—, —C(O)—Y—, —C(O)—C(O)—, or —C(O)—C(O)—Y—;

Y is oxygen, or N(R$^6$);

wherein R$^6$ is hydrogen, E, (C$_1$–C$_6$)-straight or branched alkyl, (C$_3$–C$_6$)-straight or branched alkenyl or alkynyl; or wherein R$^6$ and D are taken together with the atoms to which they are bound to form a 5 to 7 membered ring system wherein said ring optionally contains 1 to 3 additional heteroatoms independently selected from O, S, N, NH, SO, or SO$_2$; and wherein said ring is optionally benzofused;

D is hydrogen, (C$_1$–C$_7$)-straight or branched alkyl, (C$_2$–C$_7$)-straight or branched alkenyl or alkynyl, (C$_5$–C$_7$)-cycloalkyl or cycloalkenyl optionally substituted with (C$_1$–C$_6$)-straight or branched alkyl or (C$_2$–C$_7$)-straight or branched alkenyl or alkynyl, [(C$_1$–C$_7$)-alkyl]-E, [(C$_2$–C$_7$)-alkenyl or alkynyl]-E, or E;

wherein 1 to 2 of the CH$_2$ groups of said alkyl, alkenyl or alkynyl chains in D is optionally replaced by —O—, —S—, —S(O)—, —S(O$_2$)—, or —N(R$^3$);

m is 0 to 3; and x is 0 or 1;

provided that when J is hydrogen or G is selected from —S(O)$_2$—, C(O)C(O)—, SO$_2$—Y, C(O)—Y, or C(O)C(O)—Y, wherein Y is O; then D is not hydrogen.

According to a preferred embodiment, each of A and B in formula (I) is (C1–C10) straight or branched alkyl, wherein 1–2 hydrogen atoms in said alkyl are optionally substituted with E.

In another preferred embodiment, B is hydrogen.

According to a more preferred embodiment, each of A and B in formula (I) is —CH$_2$—CH$_2$—E or —CH$_2$—CH$_2$—CH$_2$—E.

According to another preferred embodiment, D in formula (I) is (C1–C7) straight or branched alkyl, E or [(C1–C6)-straight or branched alkyl]-E.

According to a more preferred embodiment, D is an aromatic monocyclic or bicyclic ring system, wherein each ring comprises 5–7 ring atoms independently selected from C, N, O or S, and wherein no more than 4 ring atoms are selected from N, O or S.

According to an even more preferred embodiment, D is phenyl or $C_1$–$C_7$ straight or branched alkyl group.

According to another preferred embodiment, E in formula (I) is a monocyclic or bicyclic aromatic ring system, wherein said ring comprises 5–7 ring atoms independently selected from C, N, O or S, and wherein 1 to 4 ring atoms are independently selected from N, O or S.

Preferred embodiments of E include phenyl, napthyl, indenyl, azulenyl, fluorenyl; anthracenyl, furyl, thienyl, pyridyl, pyrrolyl, oxazolyl, thiazolyl, imidazolyl, pyrazolyl, pyrazolinyl, pyrazolidinyl, isothiazolyl, 1,3,4-thiadiazolyl, pyridazinyl, pyrimidinyl, 1,3,5-trazinyl, 1,3,5-trithianyl, benzo[b]furanyl, benzo[b]thiophenyl, purinyl, cinnolinyl, phthalazinyl, isoxazolyl, triazolyl, oxadiazolyl, pyrimidinyl, pyrazinyl, indolinyl, indolizinyl, isoindolyl, benzimidazolyl, benzothiophenyl, quinolinyl, isoquinolinyl, quinazolinyl, quinoxalinyl, 1,8-naphthyridinyl, pteridinyl, carbazolyl, acridinyl, phnazinyl, phenothiazinyl, phenoxazinyl and benzothiazolyl, wherein E is optionally substituted as described above.

More preferred embodiments of E include phenyl, furyl, thienyl, pyridyl, pyrrolyl, oxazolyl, thiazolyl, imidazolyl, pyrazolyl, isoxazolyl, triazolyl, oxadiazolyl, pyrimidinyl, pyrazinyl, indolyl, isoindolyl, benzimidazolyl, benzothiophenyl, quinolinyl, isoquinolinyl, and benzothiazolyl, wherein E is optionally substituted as described above.

According to another preferred embodiment, J is H, methyl, ethyl or benzyl; and

K is selected from ($C_1$–$C_6$)-straight or branched alkyl, ($C_2$–$C_6$)-straight or branched alkenyl 5 or alkynyl, or cyclohexylmethyl, wherein 1 to 2 hydrogen atoms in said alkyl, alkenyl or alkynyl is optionally and independently replaced with E.

According to another preferred embodiment, J and K, taken together with the nitrogen atom, form a 5–7 membered heterocyclic ring, optionally containing up to 3 additional heteroatoms selected from O, N, S and S(O$_2$), wherein 1 to 4 hydrogen atoms in said heterocyclic ring are optionally and independently replaced with ($C_1$–$C_6$)-straight or branched alkyl, ($C_2$–$C_6$)-straight or branched alkenyl or alkynyl, oxo, hydroxyl or Z; and wherein any —CH$_2$— group said heterocyclic ring is optionally and independently replaced by —O—, —S—, —S(O)—, —S(O$_2$)—, or —N(R$^3$)—; and wherein said heterocyclic ring is optionally fused with E.

According to another preferred embodiment, K and R1, taken together with the nitrogen atom, form a 5–7 membered heterocyclic ring, optionally containing up to 3 additional heteroatoms selected from O, N, S and S(O$_2$), wherein 1 to 4 hydrogen atoms in said heterocyclic ring are optionally and independently replaced with ($C_1$–$C_6$)-straight or branched alkyl, ($C_2$–$C_6$)-straight or branched alkenyl or alkynyl, oxo, hydroxyl or Z; and wherein any —CH$_2$— group said heterocyclic ring is optionally and independently replaced by —O—, —S—, —S(O)—, —S(O$_2$)—, or —N(R$^3$)—; and wherein said heterocyclic ring is optionally fused with E.

The compounds of formula (I) may be stereoisomers, geometric isomers or stable tautomers. The invention envisions all possible isomers, such as E and Z isomers, S and R enantiomers, diastereoisomers, racemates, and mixtures of those. It is preferred that the substituent in the 2 position have the S configuration.

The compounds of the present invention may be readily prepared using known synthetic methods. For example, compounds of formula (I) may be prepared as shown below in Scheme I:

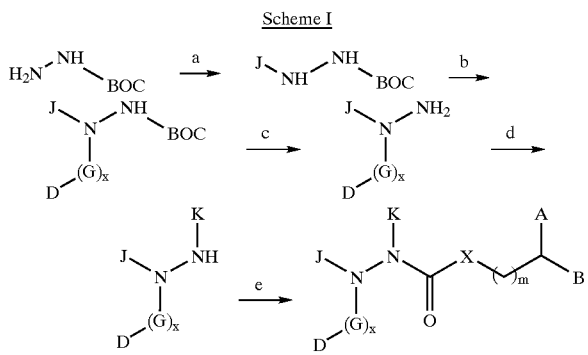

Scheme I a=J—CHO and NaCNBH$_3$, b=D—Cl or D—Br and K$_2$CO$_3$ when x=0; D—G—Cl and diisopropylethylamine when x=1; c=HCl/EtOAc or trifluoroacetic acid/CH$_2$Cl$_2$; K—CHO and NaCNBH$_3$; e=COCl$_2$ followed by the addition of the amine or alcohol of —X—(CH$_2$)$_m$—CH(A)(B).

One of skill in the art would be well aware of analogous synthetic methods to prepare the compounds of the present invention.

According to another embodiment, this invention provides compositions comprising a compound of formula. (I) and a pharmaceutically acceptable carrier.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxy methylcellulose, polyacrylates, waxes, polyethylene-polyoxypropylene block polymers, polyethylene glycol and wool fat.

In another embodiment, the composition of the present invention is comprised of a compound of formula (I), a pharmaceutically acceptable carrier, and a neurotrophic factor.

The term "neurotrophic factor," as used herein, refers to compounds which are capable of stimulating growth or proliferation of nervous tissue. Numerous neurotrophic factors have been identified in the art and any of those factors may be utilized in the compositions of this invention. These neurotrophic factors include, but are not limited to, nerve growth factor (NGF), insulin-like growth factor (IGF-1) and its active truncated derivatives such as gIGF-1 and Des(1–3) IGF-I, acidic and basic fibroblast growth factor (aFGF and bFGF, respectively), platelet-derived growth factors (PDGF), brain-derived neurotrophic factor (BDNF), ciliary neurotrophic factors (CNTF), glial cell line-derived neurotrophic factor (GDNF), neurotrophin-3 (NT-3)and neurotrophin 4/5 (NT-4/5). The most preferred neurotrophic factor in the compositions of this invention is NGF.

As used herein, the described compounds used in the compositions and methods of this invention, are defined to include pharmaceutically acceptable derivatives thereof. A "pharmaceutically acceptable derivative" denotes any pharmaceutically acceptable salt, ester, or salt of such ester, of a compound of this invention or any other compound which, upon administration to a patient, is capable of providing (directly or indirectly) a compound of this invention, or a metabolite or residue thereof, characterized by the ability to promote repair or prevent damage of neurons from disease or physical trauma.

If pharmaceutically acceptable salts of the described compounds are used, those salts are preferably derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The described compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the compositions may be formulated in an ointment such as petrolatum.

The compositions of this invention may also be administered by nasal aerosol or inhalation. Such compositions are prepared according to techniques well-known in the art of formulation and may be prepared as solutions in saline, employing benzyl alcohol or other suitable preservatives, absorption promoters to enhance bioavailability, fluorocarbons, and/or other conventional solubilizing or dispersing agents.

The amount of both a described compound and the optional neurotrophic factor that may be combined with the carrier materials to produce a single dosage form will vary depending upon the host treated and the particular mode of administration. Preferably, the compositions should be formulated so that a dosage of between 0.01–100 mg/kg body weight/day of the described compound can be administered. If a neurotrophic factor is present in the composition, then a dosage of between 0.01 $\mu$g –100 mg/kg body weight/day of the neurotrophic factor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and neurotrophic factor in the composition.

According to another embodiment, this invention provides methods for promoting repair or preventing neuronal damage or neuronal degeneration in vivo or in an ex vivo nerve cell. Such methods comprise the step of treating nerve cells with any of the compounds described above. Preferably, this method promotes repair or prevents neuronal damage in a patient, and the compound is formulated into a composition additionally comprising a pharmaceutically acceptable carrier. The amount of the compound utilized in these methods is between about 0.01 and 100 mg/kg body weight/day.

According to an alternate embodiment, the method of promoting repair or preventing neuronal damage comprises the additional step of treating nerve cells with a neurotrophic factor, such as those contained in the compositions of this invention. This embodiment includes administering the compound and the neurotrophic agent in a single dosage form or in separate, multiple dosage forms. If separate dosage forms are utilized, they may be administered concurrently, consecutively or within less than about 5 hours of one another.

Preferably, the methods of this invention are used to stimulate axonal growth in nerve cells. The compounds are, therefore, suitable for treating or preventing neuronal damage caused by a wide variety of diseases or physical traumas. These include, but are not limited to, Alzheimer's disease, Parkinson's disease, ALS, Huntington's disease, Tourette's syndrome, stroke and ischemia associated with stroke, neural paropathy, other neural degenerative diseases, motor neuron diseases, sciatic crush, spinal cord injuries and facial nerve crush.

In a particularly preferred embodiment of the invention, the method is used to treat a patient suffering from trigeminal neuralgia, glosspharyngeal neuralgia, Bell's Palsy, myasthenia gravis, muscular dystrophy, muscle injury, progressive muscular atrophy, progressive bulbar inherited muscular atrophy, herniated, ruptured, or prolapsed invertebrae disk syndrome's, cervical spondylosis, plexus disorders, thoracic outlet destruction syndromes, peripheral neuropathies, such as those caused by lead, dapsone, ticks, or porphyria, other peripheral myelin disorders, Alzheimer's disease, Gullain-Barre syndrome, Parkinson's disease and other Parkinsonian disorders, ALS, Tourette's syndrome, multiple sclerosis, other central myelin disorders, stroke and ischemia associated with stroke, neural paropathy, other neural degenerative diseases, motor neuron diseases, sciatic crush, neuropathy associated with diabetes, spinal cord injuries, facial nerve crush and other trauma, chemotherapy- and other medication-induced neuropathies, and Huntington's disease.

More preferably, the compositions of the present invention are used for treating Parkinson's disease, amylotrophic lateral sclerosis, Alzheimer's disease, stroke, neuralgias, muscular atrophies, and Guillain-Barré syndrome.

For use of the compounds according to the invention as medications, they are administered in the form of a preparation containing not only the active ingredient but also carriers, auxiliary substances, and/or additives suitable for enteric or parenteral administration. Administration can be oral or sublingual as a solid in the form of capsules or tablets, as a liquid in the form of solutions, suspensions, elixirs, aerosols or emulsions, or rectal in the form of suppositories, or in the form of solutions for injection which can be given subcutaneously, intramuscularly, or intravenously, or which can be given topically or intrathecally. Auxiliary substances for the desired medicinal formulation include the inert organic and inorganic carriers known to those skilled in the art, such as water, gelatin, gum arabic, lactose, starches, magnesium stearate, talc, vegetable oils, polyalkylene glycols, etc. The medicinal formulations may also contain preservatives, stabilizers, wetting agents, emulsifiers, or salts to change the osmotic pressure or as buffers.

Solutions or suspensions for injection are suitable for parenteral administration, and especially aqueous solutions of the active compounds in polyhydroxy-ethoxylated castor oil.

Surface-active auxiliary substances such as salts of gallic acid, animal or vegetable phospholipids, or mixtures of them, and liposomes or their components, can be used as carrier systems.

The neurotrophic effect of the compounds of formula (I) of the present invention and their physiologically acceptable salts can be determined by the methods of W. E. Lyons et al., *Proc. Natl. Acad. Sci. USA*, Vol. 91, pp. 3191–3195 (1994) and W. E. Lyons et al., *Proc. Natl. Acad. Sci. USA*, Vol. 91, pages 3191–3195 (1994).

In order that this invention be more fully understood, the following examples are set forth. These examples are for the purpose of illustration only and are not to be construed as limiting the scope of the invention in any way.

EXAMPLE 1

Compound 103–109

Compounds 103–109 have the following general formula:

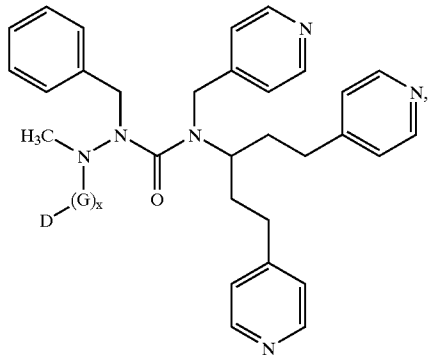

wherein —(G)$_x$—D is as follows:
- —CH$_3$— compound 103
- —CH$_2$CH$_3$— compound 104
- —C(O)—CH$_3$— compound 105
- —CH$_2$—Ph— compound 106
- —C(O)—Ph— compound 107
- —C(O)—O—CH$_2$—Ph— compound 108
- —C(O)—C(O)—Ph— compound 109, wherein Ph is phenyl.

EXAMPLE 2

Compound 110–116

Compounds 110–116 have the following general formula:

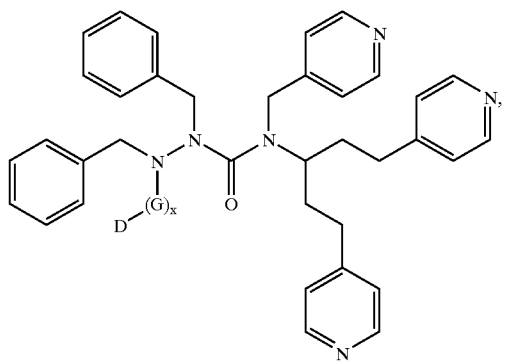

wherein —(G)$_x$—D is as follows:
- —CH$_3$— compound 110
- —CH$_2$CH$_3$— compound 111
- —C(O)—CH$_3$— compound 112
- —CH$_2$—Ph— compound 113
- —C(O)—Ph— compound 114
- —C(O)—O—CH$_2$—Ph— compound 115
- —C(O)—C(O)—Ph— compound 116, wherein Ph is phenyl.

EXAMPLE 3

Compound 117–123

Compounds 117–123 have the following general formula:

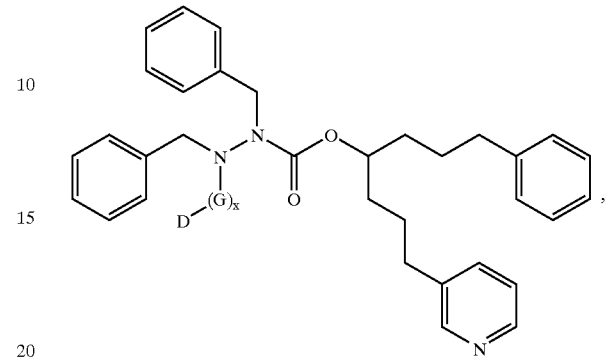

wherein —(G)$_x$—D is as follows:
- —CH$_3$— compound 117
- —CH$_2$CH$_3$— compound 118
- —C(O)—CH$_3$— compound 119
- —CH$_2$—Ph— compound 120
- —C(O)—Ph— compound 121
- —C(O)—O—CH$_2$—Ph— compound 122
- —C(O)—C(O)—Ph— compound 123, wherein Ph is phenyl.

EXAMPLE 4

Compound 124–130

Compounds 124–130 have the following general formula:

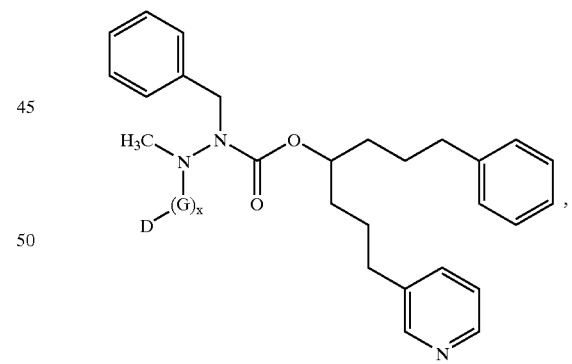

wherein —(G)$_x$—D is as follows:
- —CH$_3$— compound 124
- —CH$_2$CH$_3$— compound 125
- —C(O)—CH$_3$— compound 126
- —CH$_2$—Ph— compound 127
- —C(O)—Ph— compound 128
- —C(O)—O—CH$_2$—Ph— compound 129
- —C(O)—C(O)—Ph— compound 130, wherein Ph is phenyl.

EXAMPLE 5

Compound 131–137

Compounds 131–137 have the following general formula:

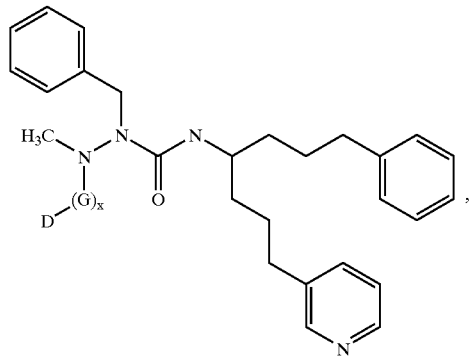

wherein —(G)$_x$—D is as follows:
- —CH$_3$— compound 131
- —CH$_2$CH$_3$— compound 132
- —C(O)—CH$_3$— compound 133
- —CH$_2$—Ph— compound 134
- —C(O)—Ph— compound 135
- —C(O)—O—CH$_2$—Ph— compound 136
- —C(O)—C(O)—Ph— compound 137, wherein Ph is phenyl.

EXAMPLE 6

Compound 138–144

Compounds 138–144 have the following general formula:

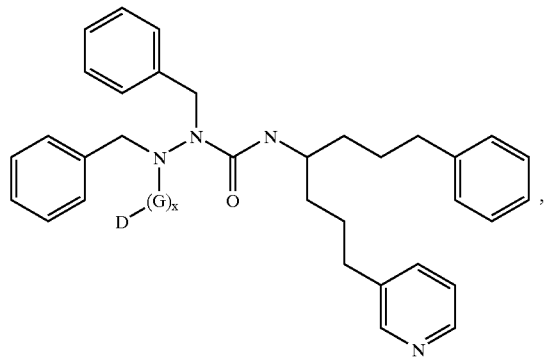

wherein —(G)$_x$—D is as follows:
- —CH$_3$— compound 138
- —CH$_2$CH$_3$— compound 139
- —C(O)—CH$_3$— compound 140
- —CH$_2$—Ph— compound 141
- —C(O)—Ph— compound 142
- —C(O)—O—CH$_2$—Ph— compound 143
- —C(O)—C(O)—Ph— compound 144, wherein Ph is phenyl.

EXAMPLE 7

Compound 145–151

Compounds 145–151 have the following general formula:

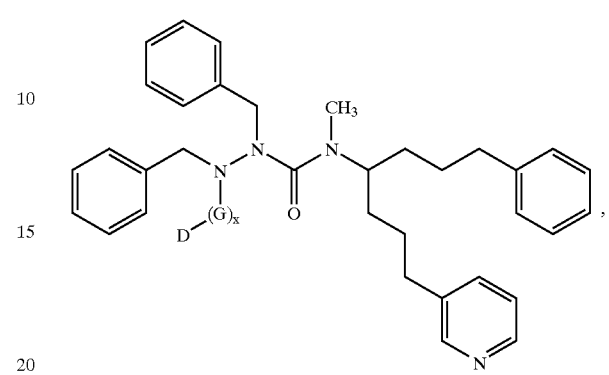

wherein —(G)$_x$—D is as follows:
- —CH$_3$— compound 145
- —CH$_2$CH$_3$— compound 146
- —C(O)—CH$_3$— compound 147
- —CH$_2$—Ph— compound 148
- —C(O)—Ph— compound 149
- —C(O)—O—CH$_2$—Ph— compound 150
- —C(O)—C(O)—Ph— compound 151, wherein Ph is phenyl.

EXAMPLE 8

Compound 152–158

Compounds 152–158 have the following general formula:

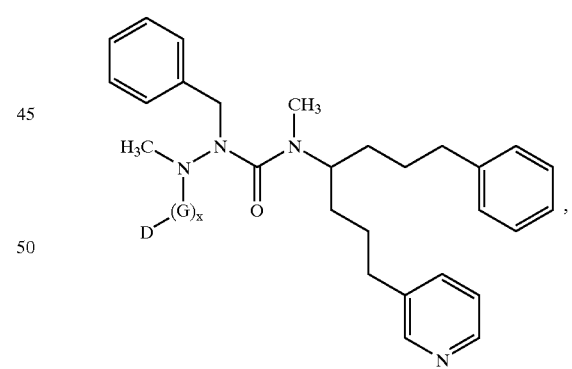

wherein —(G)$_x$—D is as follows:
- —CH$_3$— compound 152
- —CH$_2$CH$_3$— compound 153
- —C(O)—CH$_3$— compound 154
- —CH$_2$—Ph— compound 155
- —C(O)—Ph— compound 156
- —C(O)—O—CH$_2$—Ph— compound 157
- —C(O)—C(O)—Ph— compound 158, wherein Ph is phenyl.

EXAMPLE 9

Compound 159–165

Compounds 159–165 have the following general formula:

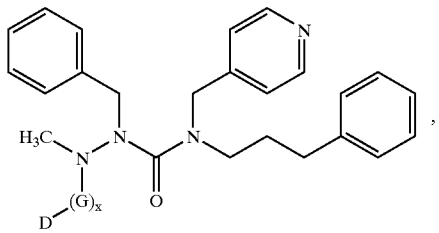

wherein —(G)$_x$—D is as follows:

- —CH$_3$— compound 159
- —CH$_2$CH$_3$— compound 160
- —C(O)—CH$_3$— compound 161
- —CH$_2$—Ph— compound 162
- —C(O)—Ph— compound 163
- —C(O)—O—CH$_2$—Ph— compound 164
- —C(O)—C(O)—Ph— compound 165, wherein Ph is phenyl.

EXAMPLE 10

Compound 166–172

Compounds 166–172 have the following general formula:

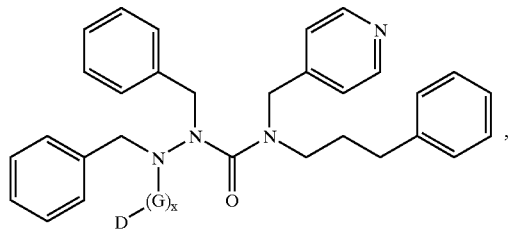

wherein —(G)$_x$—D is as follows:

- —CH$_3$— compound 166
- —CH$_2$CH$_3$— compound 167
- —C(O)—CH$_3$— compound 168
- —CH$_2$—Ph— compound 169
- —C(O)—Ph— compound 170
- —C(O)—O—CH$_2$—Ph— compound 171
- —C(O)—C(O)—Ph— compound 172, wherein Ph is phenyl.

EXAMPLE 11

Compound 173–179

Compounds 173–179 are made according to scheme and have the following general formula:

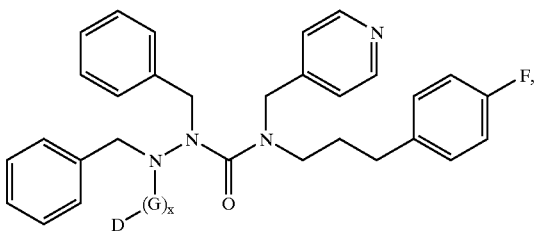

wherein —(G)$_x$—D is as follows:

- —CH$_3$— compound 173
- —CH$_2$CH$_3$— compound 174
- —C(O)—CH$_3$— compound 175
- —CH$_2$—Ph— compound 176
- —C(O)—Ph— compound 177
- —C(O)—O—CH$_2$—Ph— compound 178
- —C(O)—C(O)—Ph— compound 179, wherein Ph is phenyl.

EXAMPLE 12

Compound 180–186

Compounds 180–186 are made according to scheme and have the following general formula:

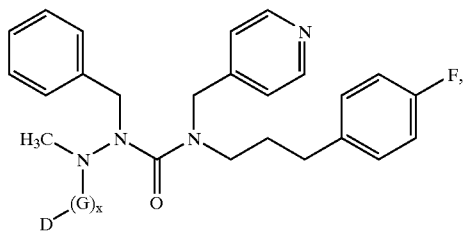

wherein —(G)$_x$—D is as follows:

- —CH$_3$— compound 180
- —CH$_2$CH$_3$— compound 181
- —C(O)—CH$_3$— compound 182
- —CH$_2$—Ph— compound 183
- —C(O)—Ph— compound 184
- —C(O)—O—CH$_2$—Ph— compound 185
- —C(O)—C(O)—Ph— compound 186, wherein Ph is phenyl.

EXAMPLE 13

Compound 187–192

Compounds 180–186 are made according to scheme and have the following general formula:

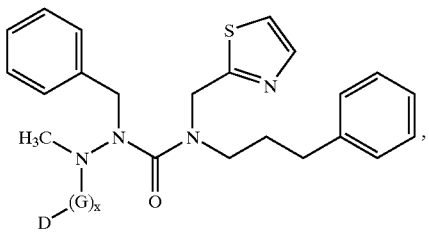

wherein —(G)$_x$—D is as follows:
- —CH$_3$— compound 187
- —CH$_2$CH$_3$— compound 188
- —C(O)—CH$_3$— compound 189
- —CH$_2$—Ph— compound 190
- —C(O)—Ph— compound 191
- —C(O)—O—CH$_2$—Ph— compound 192
- —C(O)—C(O)—Ph— compound 193, wherein Ph is phenyl.

EXAMPLE 14

Compound 193–199

Compounds 180–186 are made according to scheme and have the following general formula:

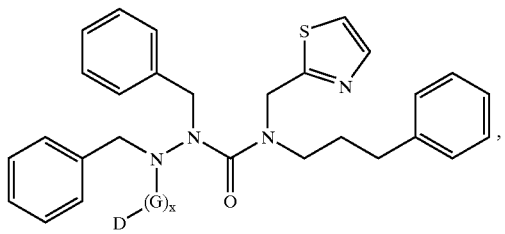

wherein —(G)$_x$—D is as follows:
- —CH$_3$— compound 193
- —CH$_2$CH$_3$— compound 194
- —C(O)—CH$_3$— compound 195
- —CH$_2$—Ph— compound 196
- —C(O)—Ph— compound 197
- —C(O)—O—CH$_2$—Ph— compound 198
- —C(O)—C(O)—Ph— compound 199, wherein Ph is phenyl.

While we have described a number of embodiments of this invention, it is apparent that our basic constructions may be altered to provide other embodiments which utilize the products, processes and methods of this invention. Therefore, it will be appreciated that the scope of this invention is to be defined by the appended claims, rather than by the specific embodiments which have been presented by way of example.

What is claimed is:

1. A compound having formula (I):

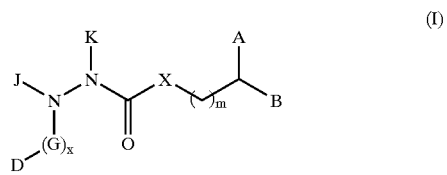

or a pharmaceutically acceptable salt thereof, wherein:

one of A and B is a (C$_1$–C$_{10}$)-straight or branched alkyl substituted with pyridine or a (C$_2$–C$_{10}$)-straight or branched alkenyl or alkynyl substituted with pyridine; and the other of A and B (C$_1$–C$_{10}$)-straight or branched alkyl substituted with phenyl or a (C$_2$–C$_{10}$)-straight or branched alkenyl or alkynyl substituted with phenyl;

X is NR$^1$;

R$^1$ is E, (C$_1$–C$_{10}$)-straight or branched alkyl, (C$_2$–C$_{10}$)-straight or branched alkenyl or alkynyl, or (C$_5$–C$_7$)-cycloalkyl or cycloalkenyl; wherein 1 or 2 hydrogen atoms in said alkyl, alkenyl or alkynyl are optionally and independently replaced with E, (C$_5$–C$_7$)-cycloalkyl or cycloalkenyl; and wherein 1 to 2 of the —CH$_2$— groups in said alkyl, alkenyl, or alkynyl groups is optionally and independently replaced by —O—, —S—, —S(O)—, —S(O)$_2$—, =N—, —N= or —N(R$^3$)—;

or R$^1$ is hydrogen;

wherein R$^3$ is selected from hydrogen, (C$_1$–C$_4$)-straight or branched alkyl, (C$_3$–C$_4$)-straight or branched alkenyl or alkynyl, or (C$_1$–C$_4$) bridging alkyl, wherein a bridge is formed between the nitrogen atom to which said R$^3$ is bound and any carbon atom of said alkyl, alkenyl or alkynyl to form a ring, and wherein said ring is optionally benzofused;

wherein E is a saturated, partially saturated or unsaturated, or aromatic monocyclic or bicyclic ring system, wherein each ring comprises 5 to 7 ring atoms independently selected from C, N, O or S; and wherein no more than 4 ring atoms are selected from N, O or S;

wherein 1 to 4 hydrogen atoms in E are optionally and independently replaced with halogen, hydroxyl, hydroxymethyl, nitro, SO$_3$H, trifluoromethyl, trifluoromethoxy, (C$_1$–C$_6$)-straight or branched alkyl, (C$_2$–C$_6$)-straight or branched alkenyl, O—[(C$_1$–C$_6$)-straight or branched alkyl], O—[(C$_3$–C$_6$)-straight or branched alkenyl], (CH$_2$)$_n$—N(R$^4$)(R$^5$), (CH$_2$)$_n$—NH $(R^4)$—$(CH_2)_n$—Z, $(CH_2)_n$—N($R^4$—$(CH_2)_n$—Z)($R^5$—$(CH_2)_n$—Z), $(CH_2)_n$—Z, O—$(CH_2)_n$—Z, $(CH_2)_n$—O—Z, S—$(CH_2)_n$—Z, CH=CH—Z, 1,2-methylenedioxy, C(O)OH, C(O)O—[($C_1$-$C_6$)-straight or branched alkyl], C(O)O—$(CH_2)_n$—Z or C(O)—N($R^4$)($R^5$);

wherein each of $R^4$ and $R^5$ are independently hydrogen, ($C_1$-$C_6$)-straight or branched alkyl, ($C_3$-$C_5$)-straight or branched alkenyl, or wherein $R^4$ and $R^5$, when bound to the same nitrogen atom, are taken together with the nitrogen atom to form a 5 or 6 membered ring, wherein said ring optionally contains 1 to 3 additional heteroatoms independently selected from N, O or S;

wherein said alkyl, alkenyl or alkynyl groups in $R_4$ and $R_5$ are optionally substituted with Z, each n is independently 0 to 4;

each Z is independently selected from a saturated, partially saturated or unsaturated, monocyclic or bicyclic ring system, wherein each ring comprises 5 to 7 ring atoms independently selected from C, N, O or S; and wherein no more than 4 ring atoms are selected from N, O or S;

wherein 1 to 4 hydrogen atoms in Z are optionally and independently replaced with halo, hydroxy, nitro, cyano, C(O)OH, ($C_1$-$C_3$)-straight or branched alkyl, O—($C_1$-$C_3$)-straight or branched alkyl, C(O)O—[($C_1$-$C_3$)-straight or branched alkyl], amino, NH[($C_1$-$C_3$)-straight or branched alkyl], or N—[($C_1$-$C_3$)-straight or branched alkyl]$_2$;

J is selected from hydrogen, ($C_1$-$C_6$)-straight or branched alkyl, ($C_2$-$C_6$)-straight or branched alkenyl or alkynyl, or cyclohexylmethyl, wherein 1 to 2 hydrogen atoms in said alkyl, alkenyl or alkynyl is optionally and independently replaced with E;

K is ($C_1$-$C_{10}$)-straight or branched alkyl substituted with phenyl or a ($C_2$-$C_{10}$)-straight or branched alkenyl or alkynyl substituted with phenyl;

wherein J and K are optionally and independently substituted with up to 3 substituents selected from halogen, OH, O—($C_1$-$C_6$)-alkyl, O—$(CH_2)$n—Z, $NO_2$, C(O)OH, C(O)—O—($C_1$-$C_6$)-alkyl, C(O)$NR^4R^5$, $NR^4R^5$ and $(CH_2)_n$—Z;

G, when present, is —S(O)$_2$—, —C(O)—, —S(O)$_2$—Y—, —C(O)—Y—, —C(O)—C(O)—, or —C(O)—C(O)—Y—;

Y is oxygen, or N($R^6$);

wherein $R^6$ is hydrogen, E, ($C_1$-$C_6$)-straight or branched alkyl, ($C_3$-$C_6$)-straight or branched alkenyl or alkynyl; or wherein $R^6$ and D are taken together with the atoms to which they are bound to form a 5 to 7 membered ring system wherein said ring optionally contains 1 to 3 additional heteroatoms independently selected from O, S, N, NH, SO, or $SO_2$; and wherein said ring is optionally benzofused;

D is a saturated, partially saturated or unsaturated, or aromatic monocyclic or bicyclic ring system, wherein each ring comprises 5 to 7 carbon ring atoms;

wherein 1 to 4 hydrogen atoms in D are optionally and independently replaced with halogen, hydroxyl, hydroxymethyl, nitro, $SO_3H$, trifluoromethyl, trifluoromethoxy, ($C_1$-$C_6$)-straight or branched alkyl, ($C_2$-$C_6$)-straight or branched alkenyl, O—[($C_1$-$C_6$)-straight or branched alkyl], O—[($C_3$-$C_6$)-straight or branched alkenyl], $(CH_2)_n$—N($R^4$)($R^5$), $(CH_2)_n$—NH($R^4$)—$(CH_2)_n$—Z, $(CH_2)_n$—N($R^4$—$(CH_2)_n$—Z)($R^5$—$(CH_2)_n$—Z), $(CH_2)_n$Z, O—$(CH_2)_n$—Z, $(CH_2)_n$—O—Z, S—$(CH_2)_n$—Z, CH=CH—Z, 1,2-methylenedioxy, C(O)OH, C(O)O—[($C_1$-$C_6$)-straight or branched alkyl], C(O)O—$(CH_2)_n$—Z or C(O)—N($R^4$)($R^5$);

m is 0 to 3; and x is 0 or 1; provided that when J is hydrogen or G is selected from S(O)$_2$—, C(O)C(O)—, $SO_2$—Y, C(O)—Y, or C(O)C(O)—Y, wherein Y is O; then D is not hydrogen.

2. The compound according to claim 1, wherein:

one of A and B is —$CH_2$—$CH_2$-pyridyl or —$CH_2$—$CH_2$—$CH_2$-pyridyl; and the other of A and B is —$CH_2$—$CH_2$-phenyl or —$CH_2$—$CH_2$—$CH_2$-phenyl;

wherein 1 to 4 hydrogen atoms in said pyridyl or phenyl is optionally and independently replaced with halogen, hydroxyl, hydroxymethyl, nitro, $SO_3H$, trifluoromethyl, trifluoromethoxy, ($C_1$-$C_6$)-straight or branched alkyl, ($C_2$-$C_6$)-straight or branched alkenyl, O—[($C_1$-$C_6$)-straight or branched alkyl], O—[($C_3$-$C_6$)-straight or branched alkenyl], $(CH_2)_n$—N($R^4$)($R^5$), $(CH_2)_n$—NH($R^4$)—$(CH_2)_n$—Z, $(CH_2)_n$—N($R^4$—$(CH_2)_n$—Z)($R^5$—$(CH_2)_n$—Z), $(CH_2)_n$—Z, O—$(CH_2)_n$—Z, $(CH_2)_n$—O—Z, S—$(CH_2)_n$—Z, CH=CH—Z, 1,2-methylenedioxy, C(O)OH, or C(O)—N($R^4$)($R^5$)].

3. The compound according to claim 1 or 2, wherein D is an aromatic monocyclic or bicyclic ring system, wherein each ring comprises 5 to 7 ring carbon atoms.

4. The compound according to claim 3, wherein:

D is phenyl; and x is 1.

5. The compound according to claim 4, wherein G is —C(O)C(O)—.

6. The compound according to claim 4, wherein G is —$SO_2$—.

7. The compound according to claim 4, wherein G is —C(O)—.

8. The compound according to claim 4, wherein G is —C(O)Y—.

9. The compound according to claim 1 or 2, wherein:

x is O;

D is phenyl.

10. A pharmaceutical composition comprising a compound according to claim 1 and a pharmaceutically effective carrier.

11. A compound selected from Table A below:

TABLE A

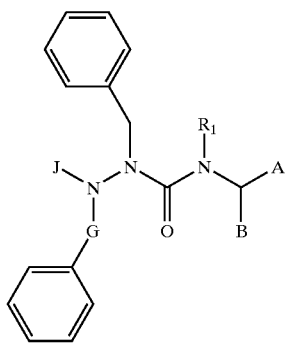

| Compd. No. | A | B | R¹ | J | G |
|---|---|---|---|---|---|
| 134 | phenylpropyl | (pyrid-3-yl)-propyl | H | $CH_3$ | —$CH_2$— |
| 135 | phenylpropyl | (pyrid-3-yl)-propyl | H | $CH_3$ | —C(O)— |
| 136 | phenylpropyl | (pyrid-3-yl)-propyl | H | $CH_3$ | —C(O)—O—$CH_2$— |
| 137 | phenylpropyl | (pyrid-3-yl)-propyl | H | $CH_3$ | —C(O)—C(O)— |
| 141 | phenylpropyl | (pyrid-3-yl)-propyl | H | benzyl | —$CH_2$— |
| 142 | phenylpropyl | (pyrid-3-yl)-propyl | H | benzyl | —C(O)— |
| 143 | phenylpropyl | (pyrid-3-yl)-propyl | H | benzyl | —C(O)—O—$CH_2$— |
| 144 | phenylpropyl | (pyrid-3-yl)-propyl | H | benzyl | —C(O)—C(O)— |
| 148 | phenylpropyl | (pyrid-3-yl)-propyl | $CH_3$ | benzyl | —$CH_2$— |
| 149 | phenylpropyl | (pyrid-3-yl)-propyl | $CH_3$ | Benzyl | —C(O)— |
| 150 | phenylpropyl | (pyrid-3-yl)-propyl | $CH_3$ | benzyl | —C(O)—O—$CH_2$— |
| 151 | phenylpropyl | (pyrid-3-yl)-propyl | $CH_3$ | Benzyl | —C(O)—C(O)— |
| 155 | phenylpropyl | (pyrid-3-yl)-propyl | $CH_3$ | $CH_3$ | —$CH_2$— |
| 156 | phenylpropyl | (pyrid-3-yl)-propyl | $CH_3$ | $CH_3$ | —C(O)— |
| 157 | phenylpropyl | (pyrid-3-yl)-propyl | $CH_3$ | $CH_3$ | —C(O)—O—$CH_2$— |
| 158 | phenylpropyl | (pyrid-3-yl)-propyl | $CH_3$ | $CH_3$ | —C(O)—C(O)—. |

12. A pharmaceutical composition according claim 10, comprising a compound according to claim 11 a pharmaceutically acceptable carrier.

* * * * *